US010954278B2

(12) United States Patent
Murugesan et al.

(10) Patent No.: US 10,954,278 B2
(45) Date of Patent: Mar. 23, 2021

(54) PEPTIDES FOR THE TREATMENT OF RESORPTIVE BONE DISEASE

(71) Applicant: University of New Brunswick, Fredericton (CA)

(72) Inventors: Alli Murugesan, Saint John (CA); Anthony Reiman, Saint John (CA)

(73) Assignee: University of New Brunswick, Fredericton (CA)

(*) Notice: Subject to any disclaimer, the term of this patent is extended or adjusted under 35 U.S.C. 154(b) by 0 days.

(21) Appl. No.: 15/773,065

(22) PCT Filed: Nov. 2, 2016

(86) PCT No.: PCT/CA2016/051273
§ 371 (c)(1),
(2) Date: May 2, 2018

(87) PCT Pub. No.: WO2017/075702
PCT Pub. Date: May 11, 2017

(65) Prior Publication Data
US 2018/0327467 A1   Nov. 15, 2018

Related U.S. Application Data

(60) Provisional application No. 62/249,471, filed on Nov. 2, 2015.

(51) Int. Cl.
*A61K 38/10* (2006.01)
*C07K 14/47* (2006.01)
*A61P 19/08* (2006.01)
*A61K 38/00* (2006.01)

(52) U.S. Cl.
CPC .......... *C07K 14/4703* (2013.01); *A61K 38/10* (2013.01); *C07K 14/47* (2013.01); *A61K 38/00* (2013.01)

(58) Field of Classification Search
None
See application file for complete search history.

(56) References Cited

U.S. PATENT DOCUMENTS

| 7,119,168 | B2 | 10/2006 | Steeves et al. | |
| 7,273,850 | B2 | 9/2007 | Steeves et al. | |
| 2011/0071089 | A1* | 3/2011 | Stewart | C07K 14/4703 514/18.9 |

FOREIGN PATENT DOCUMENTS

| WO | 2009114943 A1 | 9/2009 |
| WO | 2014/040178 A1 | 3/2014 |

OTHER PUBLICATIONS

Feng et al., "Disorders of Bone Remodeling," Annu. Rev. Pathol. Mech. Dis. 6:121-45 (2011) (Year: 2011).*
Rodan et al., "Therapeutic approaches to bone diseases," Science 289:1508-1514 (2000) (Year: 2000).*
Chen et al., "Knockout of TRPV6 Causes Osteopenia in Mice by Increasing Osteoclastic Differentiation and Activity," Cell Physiol Biochem 33:796-809 (2014) (Year: 2014).*
Alli Murugean et al.; Anonymous: "Abstract 3791:TRPV6 Calcium Channel Peptide Antagonists as Novel Antimyeloma and Antiresorptive Agents | Cancer Research"; Apr. 1, 2016, XP05597950, retrieved from the Internet:URL:http://cancerres.aacrjournals.org/content/76/14_Supplement/3791 (retrived on Jun. 19, 2019).
Leonard Zehr; Anonymous "In Conversation with Paul Gunn | Bio Tuesday by Kilmer Lucas", Apr. 26, 2016, XP55598362; retrieved from the Internet: URL;https://www.biotuesdays.com/features/2016/7/21/in-conversation-with-paul-gun (retrieved on Jun. 21, 2019).
Anonymous: "Peptide Antagonists of Transient Receptor Potential Vanilloid Type Calcium Channel (TRPV6) as a Potential Therapeutic Agent for Multiple Myeloma | Mitacs", Jan. 1, 2014, XP5598360; Retrieved from the Internet: URL:https://ww.mitacs.ca/en/projects/peptide-antagonists-transient-receptor-potential-vanilloid-type-calcium-channel-trpv6 (retireved on Jun. 21, 2019).
Maria B Morelli et al.; "Expression and Function of the Transient Receptor Potential Ion Channel Family in the Hematologic Malignancies"' Current Molecular Pharmacology, i Jan. 2013, pp. 137-148, XP055598363, Retrieved from the Internet: URL:http://www.eurekaselect.com/121597/article (retieved on Jun. 21, 2019).
European Search Report dated Jul. 22, 2019—European Patent Application No. 16861150.7.
Joyce A. Cramer, BS et al.; The Effect of Dosing Frequency on Compliance and Persistence with Bisphosphonate Therapy in Postmenopausal Women: A comparison of studies in the United states, the united Kingdom, and France, Clenical TVol 28, No. 10, Oct. 2006, pp. 1686-1694.
Meletios A. Dimopoulos et al.; "Osteonecrosis of the jaw in patients with multiple myeloma treated with bisphosphonates: evidence of increased risk after treatment with zoledronic acid", The hematology Journal 2006; 91 (7), pp. 968-971.
World Health Technical Report Series 921, Prevention and Management of Osteoporosis, World Health Organization, Geneva 2003.
R.B. Merrifield,; Solid-Phase Peptide Synthesis. III. An Improved Synthesis of Bradykinin, vol. 3, No. 9, Sep. 1964, From the Rockefeller Institute, New York City, Received May 1, 1964 pp. 1385-1390.
Warren Gish & David J. States; Identification of Protein Coding Regions by Database Similarity, 1993 Nature Publishing Group http://www.nature.com/naturegenetics, nature genetics vol. 3, Mar. 1993, pp. 266-272.
Thomas L. Madden et al.; Applications of Network BLAST Server, Methods in Enzymology, vol. 266, pp. 131-141.
Stephen F. Altschul et al.; Gapped BLAST and PSI-BLAST: a new generation of protein database search programs, 1997 Oxford University Press, Nucleic Acids Research, 1997, vol. 25, No. 17, pp. 3389-3402.

(Continued)

Primary Examiner — Julie Ha
Assistant Examiner — Kristina M Hellman
(74) Attorney, Agent, or Firm — Eugene F. Derényi; Fogler, Rubinoff LLP

(57) ABSTRACT

Described are methods and associated uses for the treatment of resorptive bone disease using peptides comprising all of part of the C-terminal portion of soricidin. Also described are methods and associated uses for inhibiting osteoclast activity and/or bone resorption using the peptides.

16 Claims, 8 Drawing Sheets

Specification includes a Sequence Listing.

(56) References Cited

OTHER PUBLICATIONS

Jinghui Zhang and Thomas L. Madden; PowerBLAST: A New Network BLAST Application for Interactive or Automated Sequence Analysis and Annotation,Downloaded from genome.cshlp.org on Aug. 16, 2018—Published by Cold Spring Harbor Laboratory Press, pp. 649-656.

Reyna J. Simon et al.; "Peptoids: Amodular approach to drug discovery" Proc. Nad. Acad. Sci. USA vol. 89, pp. 9367-9371, Oct. 1992 Chemistry.

Van der Eerden BC, Weissgerber P, Fratzl-Zelman N, Olausson J, Hoenderop JG, Schreuders-Koedam M, et al. The transient receptor potential channel TRPV6 is dynamically expressed in bone cells but is not crucial for bone mineralization in mice. Journal of cellular physiology. 2012;227(5):1951-9.

Lieben L, Benn BS, Ajibade D, Stockmans I, Moermans K, Hediger MA, et al. Trpv6 mediates intestinal calcium absorption during calcium restriction and contributes to bone homeostasis. Bone. 2010;47(2):301-8.

Hirnet D, Olausson J, Fecher-Trost C, Bodding M, Nastainczyk W, Wissenbach U, et al. The TRPV6 gene, cDNA and protein. Cell calcium. 2003;33(5-6):509-18.

Niemeyer BA, Bergs C, Wissenbach U, Flockerzi V, Trost C. Competitive regulation of CaT-like-mediated Ca2+ entry by protein kinase C and calmodulin. Proceedings of the National Academy of Sciences of the United States of America. 2001;98(6)3600-5.

\* cited by examiner

SEQUENCE LISTING

```
<160> NUMBER OF SEQ ID NOS: 2

<210> SEQ ID NO 1
<211> LENGTH: 13
<212> TYPE: PRT
```

```
<213> ORGANISM: Artificial Sequence
<220> FEATURE:
<223> OTHER INFORMATION: peptide

<400> SEQUENCE: 1

Lys Glu Phe Leu His Pro Ser Lys Val Asp Leu Pro Arg
1               5                   10

<210> SEQ ID NO 2
<211> LENGTH: 27
<212> TYPE: PRT
<213> ORGANISM: Artificial Sequence
<220> FEATURE:
<223> OTHER INFORMATION: Peptide

<400> SEQUENCE: 2

Glu Gly Lys Leu Ser Ser Asn Asp Thr Glu Gly Gly Leu Cys Lys Glu
1               5                   10                  15

Phe Leu His Pro Ser Lys Val Asp Leu Pro Arg
            20                  25
```

PEPTIDES FOR THE TREATMENT OF RESORPTIVE BONE DISEASE

FIELD OF THE INVENTION

The present invention relates to the treatment of bone disease, and more specifically to peptides for the treatment of resorptive bone disease.

BACKGROUND OF THE INVENTION

Bone remodeling is mediated by bone-forming osteoblasts and osteoclasts that are involved in bone resorption. Bone resorption is the process by which osteoclasts break down bone through the action of various enzymes, releasing minerals and calcium into the blood. Accelerated bone turnover brought about by increased osteoclast activity is a driving force behind age-related bone loss such as osteoporosis. Patients with multiple myeloma also show evidence of bone disease and increased osteoclastic bone resorption. For some individuals with bone disease, the loss of bone tissue is sufficiently great so as to cause mechanical failure of the bone structure and bone fractures.

Currently there are few treatment options available for resorptive bone disease. One approach is the use of bisphosphonates, which are commonly used for preventing the loss of bone mass and to treat osteoporosis. However, complex dosing guidelines often result in poor compliance with treatment (Cramer et al., Clin Ther. 2006 October; 28(10): 1686-94). Furthermore, oral bisphosphonates can cause upset stomach and inflammation and erosions of the esophagus, while intravenous treatment with bisphosphonates has been associated with osteonecrosis of the jaw (Dimopoulos et al., Haematologica. 2006 July; 91(7):968-71).

Soricidin (NCBI accession no. P0C2P6) is a fifty-four amino acid paralytic peptide isolated from the submaxilary saliva gland of the Northern Short-tailed Shrew (*Blarina brevicauda*). Previous patents have described isolation of the soricidin peptide and provided data showing that the 54-mer peptide caused paralysis and inhibited calcium uptake in two ovarian cancer cell lines (see U.S. Pat. Nos. 7,119,168 and 7,273,850, incorporated by reference herein in their entirety).

Peptides corresponding to certain C-terminal sequences of soricidin have been shown to inhibit Transient Receptor Potential Vanilloid channel 6 (TRPV6) without paralytic activity and to be useful for the treatment of cancer, including metastatic cancer (see US Patent application no. 20110071089, incorporated by reference herein in its entirety). The peptides maintain TRPV6 calcium channel binding activity without the sodium-channel binding paralytic activity of the full-length soricidin peptide.

There remains a need for novel treatments for resorptive bone diseases such as osteoporosis.

SUMMARY

In one aspect, peptides corresponding to the C-terminal end of soricidin have been determined to be useful for inhibiting osteoclast activity and bone resorption. SOR-C13 (KEFLHPSKVDLPR; SEQ ID NO: 1) and SOR-C27 (EGKLSSNDTEGGLCKEFLHPSKVDLPR; SEQ ID NO: 2) reduced levels of bone resorption and osteoclast differentiation in vitro. Peptides corresponding to the C-terminal end of soricidin as described herein are therefore expected to be useful for the treatment of resorptive bone disease and in particular diseases such as osteoporosis, Paget's disease of bone, bone metastases and bone disease associated with multiple myeloma. Previously, the effect of soricidin-derived peptides on osteoclast activity and bone resorption was unknown.

Accordingly, in one aspect there is provided a method for treating or preventing resorptive bone disease in a subject in need thereof, comprising administering to the subject a peptide comprising all or part of the amino acid sequence KEFLHPSKVDLPR (SEQ ID NO:1). Also provided is the use of a peptide comprising all or part of the amino acid sequence KEFLHPSKVDLPR (SEQ ID NO:1) for treating of preventing resorptive bone disease in a subject in need thereof. Also provided is a peptide comprising all or part of the amino acid sequence KEFLHPSKVDLPR (SEQ ID NO:1) for treating of preventing resorptive bone disease in a subject in need thereof. Also provided are methods, peptides as described herein and uses thereof for the treatment or prevention of myeloma bone disease.

In one embodiment, the peptides described herein are useful for treating or preventing resorptive bone disease in a subject in need thereof. In one embodiment, the subject has a resorptive bone disease. In one embodiment, the subject has osteoporosis, Paget's disease of bone or bone metastases. In one embodiment, the subject has resorptive bone disease associated with multiple myeloma.

In one aspect, there is provided a method for inhibiting osteoclast activity comprising contacting one or more osteoclasts with a peptide comprising all or part of the amino acid sequence KEFLHPSKVDLPR (SEQ ID NO:1). Also provided is the use of a peptide comprising all or part of the amino acid sequence KEFLHPSKVDLPR (SEQ ID NO:1) for inhibiting osteoclast activity. Also provided is a peptide comprising all or part of the amino acid sequence KEFLHPSKVDLPR (SEQ ID NO:1) for inhibiting osteoclast activity.

In one embodiment, the osteoclasts are in vivo or in vitro. In one embodiment, the osteoclasts are in contact with bone. In one embodiment, the osteoclasts are in contact with bone and contacting the osteoclasts with the peptide inhibits bone resorption. In one embodiment, the peptide inhibits osteoclast differentiation. In on embodiment, the osteoclasts express TRPV6. In one embodiment, the activity of the osteoclasts has been increased by osteoclast activating factors secreted by one or more myeloma cells.

In one aspect, the peptides described herein comprise all or part of the C-terminal portion of soricidin. For example, in one embodiment the peptide comprises at least 10 contiguous amino acids of KEFLHPSKVDLPR (SEQ ID NO: 1) or at least 10 contiguous amino acids of the C-terminal sequence of EGKLSSNDTEGGLCKEFLHPSKVDLPR (SEQ ID NO: 2). In one embodiment, the peptide consists of at least 10 contiguous amino acids of the C-terminal sequence of EGKLSSNDTEGGLCKEFLHPSKVDLPR (SEQ ID NO: 2). In one embodiment, the peptide comprises, consists essentially of, or consists of between 5 and 27 contiguous amino acids of the C-terminal sequence of EGKLSSNDTEGGLCKEFLHPSKVDLPR (SEQ ID NO: 2). In one embodiment, the peptide comprises, consists essentially of, or consists of at least 5, 6, 7, 8, 9, 10 or greater than 10 contiguous amino acids of SEQ ID NO: 1 or the C-terminus of SEQ ID NO: 1 or SEQ ID NO: 2.

In one embodiment, the peptide has at least 70%, at least 75%, at least 80%, at least 85%, at least 90%, or at least 95% identity to KEFLHPSKVDLPR (SEQ ID NO: 1) or EGKLSSNDTEGGLCKEFLHPSKVDLPR (SEQ ID NO: 2). In one embodiment, the peptide comprises, consists essentially of, or consists of the amino acid sequence KEFLHPSKVDLPR (SEQ ID NO: 1) or EGKLSSNDTEGGLCKEFLHPSKVDLPR (SEQ ID NO: 2).

In one embodiment, the peptide is a homolog, analog, mimetic, fragment or derivative of all or part of the amino acid sequence KEFLHPSKVDLPR (SEQ ID NO: 1) or EGKLSSNDTEGGLCKEFLHPSKVDLPR (SEQ ID NO: 2).

In one embodiment, the peptide comprises all or part of the amino acid sequence KEFLHPSKVDLPR (SEQ ID NO:1) and inhibits osteoclast activity. In one embodiment, the peptide comprises all or part of the amino acid sequence KEFLHPSKVDLPR (SEQ ID NO:1) and inhibits the differentiation of osteoclasts from cells such as bone marrow mononuclear cells and/or macrophages. In one embodiment, the peptide comprises all or part of the amino acid sequence KEFLHPSKVDLPR (SEQ ID NO:1) and inhibits bone resorption. In one embodiment, the peptide comprises all or part of the amino acid sequence KEFLHPSKVDLPR (SEQ ID NO:1) and inhibits the activity of Tartrate-Resistant Acid Phosphatase (TRAP) in osteoclasts. In one embodiment, the peptides comprises all or part of the amino acid sequence KEFLHPSKVDLPR (SEQ ID NO:1) and inhibits TRPV6 activity.

Also provided is the use of a peptide as described herein as an anti-resorptive agent.

Also provided is the use of a peptide comprising all or part of the amino acid sequence KEFLHPSKVDLPR (SEQ ID NO: 1) or
EGKLSSNDTEGGLCKEFLHPSKVDLPR (SEQ ID NO: 2) as described herein for the preparation of a medicament for the treatment or prevention of bone disease.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from the detailed description.

BRIEF DESCRIPTION OF THE DRAWINGS

Embodiments of the invention will now be described in relation to the drawings in which:

FIG. 1A shows hematoxylin and eosin stained osteoclasts in a representative human bone marrow section. FIG. 1B shows TRPV6 immunohistochemistry staining and a strong expression of TRPV6 proteins in osteoclasts. FIG. 1C shows TRPV6 expression observed in both myeloma cells and osteoclasts.

FIG. 2A shows a blot probed for TRPV6 protein expression using Santacruz TRPV6 antibody. FIG. 2B shows a blot probed for TRPV6 protein expression using Alomone TRPV6 antibody.

FIG. 3A shows control bone marrow mononuclear cells (BMC) treated with hM-CSF only. FIG. 3B shows BMCs treated with hRANKL and hM-CSF differentiated into large osteoclasts.

FIG. 4A shows control bone marrow mononuclear cells (BMC) treated with hM-CSF only. FIG. 4B shows BMCs treated with hRANKL and hM-CSF differentiated into large, multi-nucleated osteoclasts.

FIG. 5A shows control bone marrow mononuclear cells (BMC) treated with hM-CSF only. FIG. 5B shows BMCs treated with hRANKL and hM-CSF differentiated into large osteoclasts that strongly express TRAP.

DESCRIPTION OF VARIOUS EMBODIMENTS

Definitions

As used herein, "resorptive bone disease" refers to any condition characterized by an imbalance between osteoblast and/or osteoclast activity leading to decreased bone strength and/or bone loss. Examples of resorptive bone disease include, but are not limited to, osteoporosis, Paget's disease of bone, bone metastasis, and bone disease associated with cancers such as multiple myeloma.

As used herein, "osteoporosis" refers to a disorder characterized by an imbalance between bone resorption and bone formation leading to decreased bone strength. In one embodiment, a subject has osteoporosis when their bone mineral density is less than or equal to 2.5 standard deviations below that of a young (30-40-year-old) healthy adult reference population (see e.g. WHO Scientific Group on the Prevention and Management of Osteoporosis (2000: Geneva, Switzerland) (2003). ISBN 9241209216).

As used herein, "Paget's disease of bone" or "Paget's disease" refers to a chronic disorder that can result in enlarged and misshapen bones caused by the excessive breakdown and formation of bone, followed by disorganized bone remodeling. In one embodiment, subjects with Paget's disease of bone exhibit bone pain and/or elevated levels of alkaline phosphatase in the blood.

As used herein, "bone disease associated with multiple myeloma" refers to bone loss and/or bone lesions in a subject with multiple myeloma. In one embodiment, subjects with multiple myeloma exhibit an increase in osteoclast activity caused osteoclastic activating factors released by tumor cells.

As used herein, "osteoclast" refers to a multinucleated cell capable of resorbing mineralised bone, dentine and cartilage. In one embodiment, osteoclasts are characterized by a cytoplasm with a high concentration of vacuoles containing lysosomes filled with acid phosphatase. In one embodiment, osteoclasts express tartrate resistant acid phosphatase (TRAP) and cathepsin K.

As used herein "inhibiting osteoclast activity" refers to inhibiting the resorbing activity of osteoclasts and/or inhibiting the formation of osteoclasts. In one embodiment, inhibiting osteoclast activity includes inhibiting the differentiation of macrophages and/or bone marrow mononuclear cells into osteoclasts.

Peptides for Inhibiting Osteoclasts and Treating Resorptive Bone Disease

Figure 7:
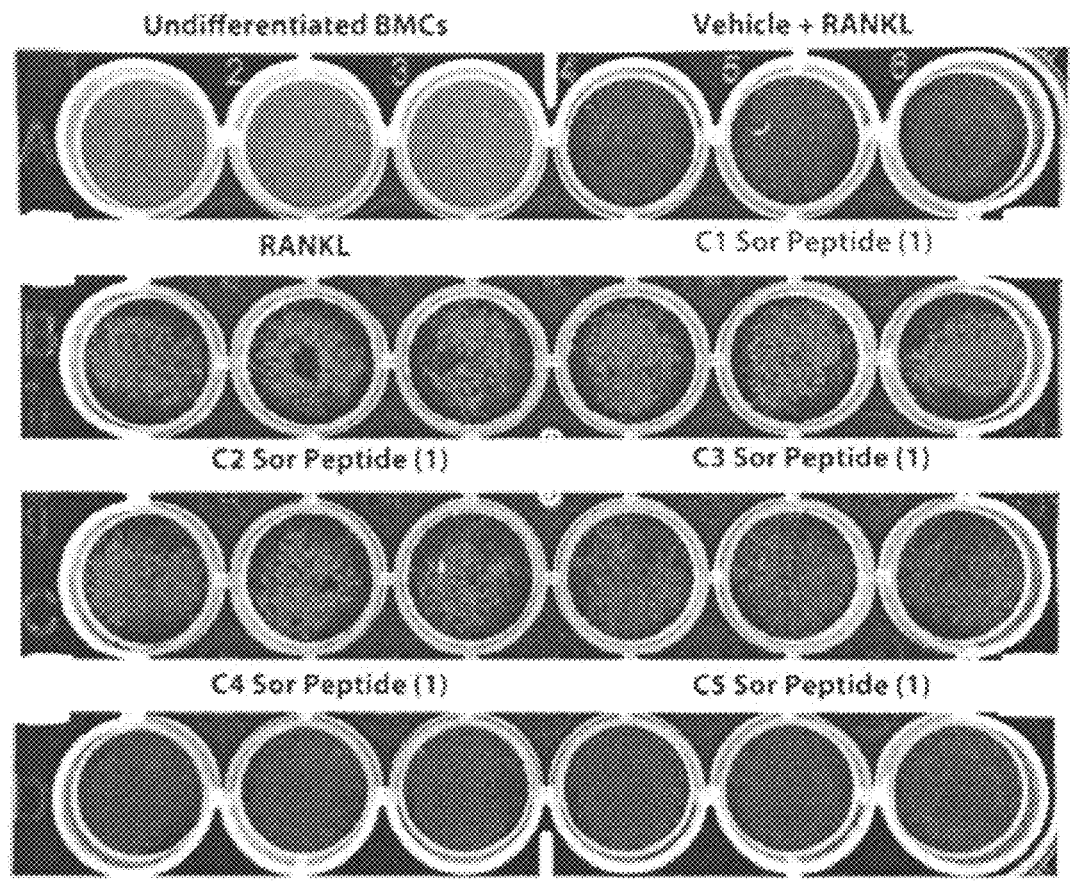
FIG. 7A shows dose-dependent Inhibition of osteoclast activity by the TRPV6 peptide antagonist SOR-C27 (SEQ ID NO: 2) (Sor Peptide (1)) on a Corning osteoassay plate.
FIG. 7B shows percentage resorption quantified using ImageJ 1.48v software and statistical analyses done with GraphPad Prism 6 software.
FIG. 7C shows TRAP enzyme activity in conditioned media of control and treated wells of the corning osteo assay plate represented in FIG. 7A. C1=1 uM; C2=10 uM; C3=50 uM; C4=100 uM; C5=150 uM.
Figure 7:
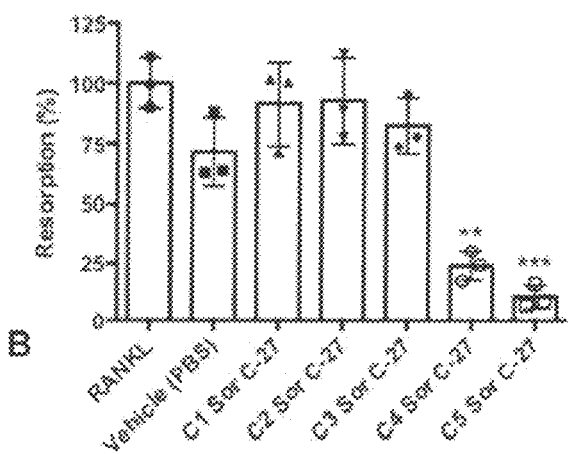
Figure 7:
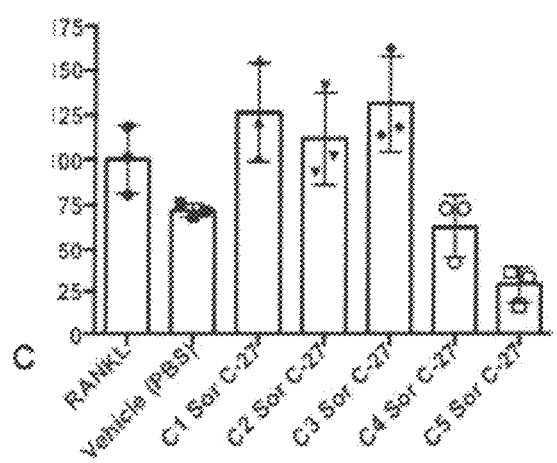
Figure 8:
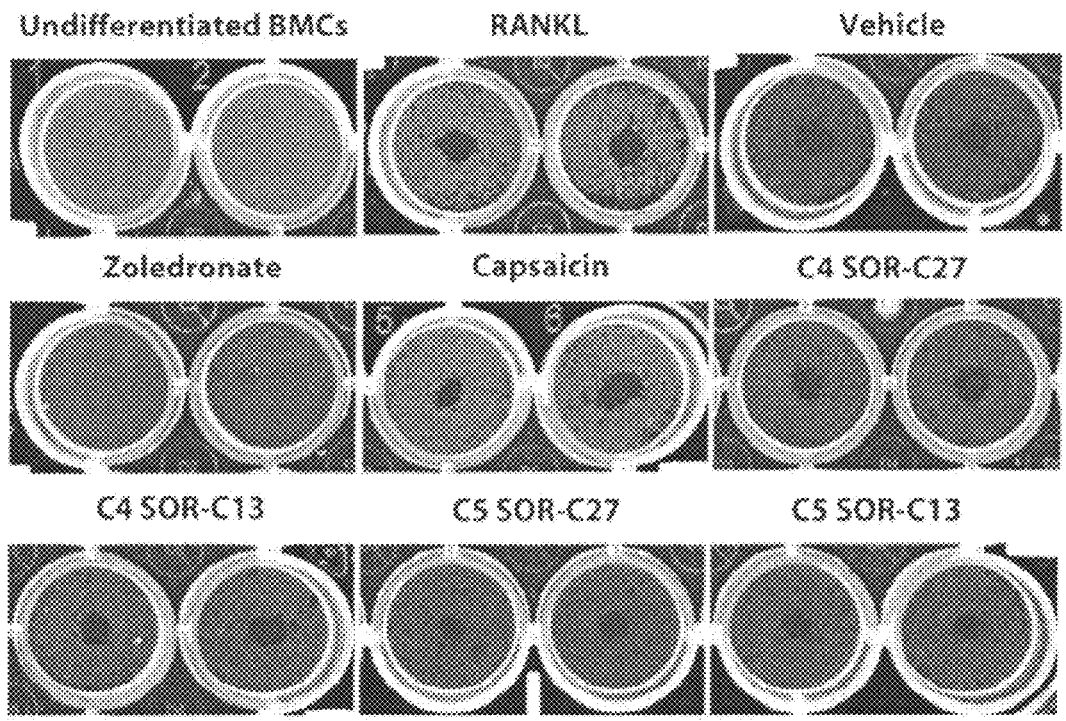
FIG. 8A shows inhibition of osteoclast activity by TRPV6 peptide antagonists SOR-C27 and SOR-C13 (SEQ ID NO: 1) on a Corning osteoassay plate.
FIG. 8B shows percentage resorption quantified using ImageJ 1.48v software and statistical analyses done with GraphPad Prism 6 software.
Figure 8:
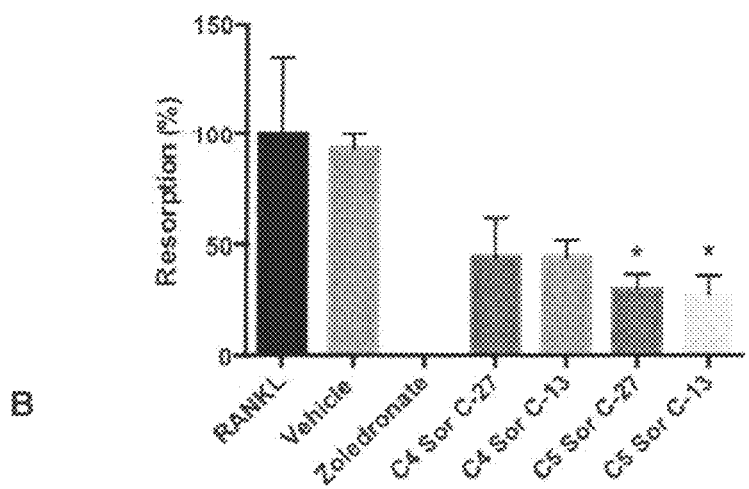

It has surprisingly been determined that peptides corresponding to the C-terminal end of Soricidin such as SOR-C13 and SOR-C27 are useful for inhibiting osteoclast activity and bone resorption. As shown in FIGS. 7 and 8, investigations into the effects of SOR-C13 and SOR-C27 using an in vitro model showed a dose-dependent decrease in bone resorption by osteoclasts. Treatment with SOR-C13 and SOR-C27 also resulted in a decrease in TRAP enzyme activity relative to controls. A number of resorptive bone diseases such as osteoporosis, Paget's disease of bone and bone disease associated with cancers are characterized by an increase in osteoclast activity such that inhibition of osteoclast activity is expected to be useful for the treatment or prevention of resorptive bone disease.

The present description therefore provides methods and uses for the treatment or prevention of bone disease in a subject in need thereof. Also provided are methods and uses for inhibiting osteoclast activity. In one embodiment, there is provided a method for treating or preventing resorptive bone disease comprising administering to the subject a peptide comprising, consisting essentially of, or consisting of all or part of KEFLHPSKVDLPR (SEQ ID NO: 1) or EGKLSSNDTEGGLCKEFLHPSKVDLPR (SEQ ID NO: 2). Also provided is the use of a peptide comprising, consisting essentially of, or consisting of all or part of KEFLHPSKVDLPR (SEQ ID NO: 1) or EGKLSSNDTEGGLCKEFLHPSKVDLPR (SEQ ID NO: 2) for the treatment or prevention of resorptive bone disease in a subject in need thereof. Also provided is a peptide comprising, consisting essentially of, or consisting of all or part of KEFLHPSKVDLPR (SEQ ID NO: 1) or EGKLSSNDTEGGLCKEFLHPSKVDLPR (SEQ ID NO: 2) for the treatment or prevention of resorptive bone disease in a subject in need thereof. In one embodiment, the peptides described herein are useful for the treatment, cure prevention or suppression of symptoms associated with resorptive bone disease.

Also provided are methods for inhibiting osteoclast activity comprising contacting one or more osteoclasts with a peptide comprising, consisting essentially of, or consisting of all or part of the amino acid sequence KEFLHPSKVDLPR (SEQ ID NO:1) or EGKLSSNDTEGGLCKEFLHPSKVDLPR (SEQ ID NO: 2). Also provided is the use of a peptide comprising, consisting essentially of, or consisting of all or part of the amino acid sequence KEFLHPSKVDLPR (SEQ ID NO:1) or EGKLSSNDTEGGLCKEFLHPSKVDLPR (SEQ ID NO: 2) for inhibiting osteoclast activity. Also provided is a peptide comprising, consisting essentially of, or consisting of all or part of the amino acid sequence KEFLHPSKVDLPR (SEQ ID NO:1) or EGKLSSNDTEGGLCKEFLHPSKVDLPR (SEQ ID NO: 2) for inhibiting osteoclast activity. Optionally, the osteoclasts are in vivo, ex vivo or in vitro.

In one embodiment, the peptide comprises from 5 to 27 contiguous amino acids of SEQ ID NO: 2. In one embodiment, the peptide comprises contiguous amino acids of SEQ ID NO: 2 starting from the N-terminal amino acid of SEQ ID NO: 2. In another embodiment, the peptide comprises contiguous amino acids starting from the C-terminal sequence of SEQ ID NO: 2. In one embodiment, the peptide comprises at least 5, 6, 7, 8, 9, 10 or greater than 10 contiguous amino acids of SEQ ID NO:2. Optionally the peptide comprises at least: 10, 11, 12, 13, 14, 15, 16, 17, 18, 19 or 20 amino acids of SEQ ID NO: 2. In one embodiment, the peptides described herein comprise, consist essentially of, or consist of the amino acid sequence KEFLHPSKVDLPR (SOR-C13) or EGKLSSNDTEGGLCKEFLHPSKVDLPR (SOR-C27).

In some embodiments, amino acids may be added to the peptides described herein. One can readily make a longer peptide by adding a variety of additional amino acids to the SOR-C27 sequences to make a peptide that could be up to, for example, 30, 35, 40 or 45 amino acids long. (e.g. additional amino acids corresponding to the soricidin amino acid sequence such as one or more of the amino acids that are immediately towards the N-terminal segment of SOR-C27 in soricidin (SILARPAELNTETCILEC; SEQ ID NO: 1), a targeting sequence, or other amino acids) or longer. In one embodiment, the peptide described herein consists of 30 or fewer, 27 or fewer, 25 or fewer, 20 or fewer, 15 or fewer, 13 or fewer, 11 or fewer, 9 or fewer, or 7 or fewer amino acids.

The peptides described herein optionally include analogs of the aforementioned peptides. Analogs of the peptides of the invention optionally include, but are not limited to an amino acid sequence containing one or more amino acid substitutions, insertions, deletions and/or mutations. Amino acid substitutions may be of a conserved or non-conserved nature. Conserved amino acid substitutions involve replacing one or more amino acids of the peptides of the invention with amino acids of similar charge, size, and/or hydrophobicity characteristics. When only conserved substitutions are made, the resulting analog should be functionally equivalent. Non-conserved substitutions involve replacing one or more amino acids of the amino acid sequence with one or more amino acids that possess dissimilar charge, size, and/or hydrophobicity characteristics. The analog is optionally a peptoid, which is an N-substituted polyglycine with amino acid R groups attached at the N atom. Another analog is optionally a peptide synthesized from D-amino acids rather than the natural L-amino acids.

One or more amino acid insertions are optionally introduced into the peptides described herein such as SOR-C13 or SOR-C27. Amino acid insertions may consist of single amino acid residues or sequential amino acids ranging for example from 2 to 15 amino acids in length.

Deletions consist of the removal of one or more amino acids, or discrete portions from the amino acid sequence of the peptide. The deleted amino acids may or may not be contiguous.

Analogs of a peptide of the invention are optionally prepared by introducing mutations in a nucleotide sequence encoding the peptide. Mutations in nucleotide sequences constructed for expression of analogs of a protein of the invention preserve the reading frame of the coding sequences. Furthermore, the mutations will preferably not create complementary regions that could hybridize to produce secondary mRNA structures such as loops or hairpins, which could adversely affect translation of the mRNA.

Mutations are optionally introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures are employed to provide an altered gene having particular codons altered according to the substitution, deletion, or insertion required. Deletion or truncation of a peptide of the invention is also readily achieved by utilizing convenient restriction endonuclease sites adjacent to the desired deletion. Subsequent to restriction, overhangs may be filled in, and the DNA re-ligated. Exemplary methods of making the alterations set forth above are disclosed by Sambrook et al. (Sambrook J et al. 2000. Molecular Cloning: A Laboratory Manual (Third Edition), Cold Spring Harbor Laboratory Press).

In addition, peptides and/or analogs useful for the purposes of the present invention are readily prepared by chemical synthesis using techniques well known in the chemistry of proteins such as solid phase synthesis (Merrifield, 1964, J. Am. Chem. Assoc. 85:2149-2154) or synthesis in homogenous solution (Houbenweyl, 1987, Methods of Organic Chemistry, ed. E. Wansch, Vol. 15 I and II, Thieme, Stuttgart). The peptides of the invention also include those having sequence identity to a peptide of the invention, mutated peptides and/or truncations thereof as described herein.

Other peptides suitable for the methods and uses of the present invention optionally comprise, consist essentially of or consist of an amino acid sequence with at least: 30%, 40%, 50%, 60%, 70%, 75%, 80%, 85%, 90% or 95% sequence identity to all or part of SEQ ID NO:1 or SEQ ID NO:2 described herein that inhibit osteoclast activity and/or decrease bone resorption levels. In one embodiment, the peptide has at least 70%, at least 75%, at least 80%, at least 85%, at least 90% or at least 95% sequence identity to the amino acid sequence KEFLHPSKVDLPR (SOR-C13) or EGKLSSNDTEGGLCKEFLHPSKVDLPR (SOR-C27). Sequence identity is typically assessed by the BLAST version 2.1 program-advanced search (parameters as above; Altschul, S. F., Gish, W., Miller, W., Myers, E. W. & Lipman, D. J. (1990) "Basic local alignment search tool." J. Mol. Biol. 215:403-410). BLAST is a series of programs that are available online through the U.S. National Center for Biotechnology Information (National Library of Medicine Building 38A Bethesda, Md. 20894) The advanced Blast search is set to default parameters. References for the Blast Programs include: Altschul, S. F., Gish, W., Miller, W., Myers, E. W. & Lipman, D. J. (1990) "Basic local alignment search tool." J. Mol. Biol. 215:403-410; Gish, W. & States, D. J. (1993) "Identification of protein coding regions by database similarity search." Nature Genet. 3:266-272.; Madden, T. L., Tatusov, R. L. & Zhang, J. (1996) "Applications of network BLAST server" Meth. Enzymol. 266:131-141; Altschul, S. F., Madden, T. L., Schaffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402); Zhang, J. & Madden, T. L. (1997) "PowerBLAST: A new network BLAST application for interactive or automated sequence analysis and annotation." Genome Res. 7:649-656).

In one embodiment, peptides suitable for the methods and uses of described herein are peptide mimetics. In one embodiment, the peptide mimetics are based on all or part of KEFLHPSKVDLPR (SEQ ID NO: 1) or EGKLSSNDTEGGLCKEFLHPSKVDLPR (SOR-C27). "Peptide mimetics" are structures which serve as substitutes for peptides in interactions between molecules (See Morgan et al. (1989), Ann. Reports Med. Chem. 24:243-252 for a review). Peptide mimetics include synthetic structures which optionally contain amino acids and/or peptide bonds but retain the structural and functional features of a peptide, or enhancer or inhibitor of the invention. Peptide mimetics also include peptoids, oligopeptoids (Simon et al. (1972) Proc. Natl. Acad, Sci USA 89:9367); and peptide libraries containing peptides of a designed length representing all possible sequences of amino acids corresponding to a peptide of the invention.

Peptide mimetics are designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of inhibitor peptide secondary structures. These structures can model the 3-dimensional orientation of amino acid residues into the known secondary conformations of proteins. Peptides may also be used which are oligomers of N-substituted amino acids and can be used as motifs for the generation of chemically diverse libraries of novel molecules.

In one embodiment, the peptides described herein are for use or administered to a subject for the treatment of resorptive bone disease and/or to inhibit osteoclast activity. In one embodiment, the peptides described herein are for use or administered to a subject to reduce osteoclast formation.

The term "subject" as used herein includes all members of the animal kingdom and is preferably a mammal, such as human. Administering a peptide to a subject includes both in vivo and ex vivo administrations. In a preferred embodiment, the subject is a human. In one embodiment, the subject has osteoporosis, Paget's disease of bone, or bone disease associated with cancer. In one embodiment, the subject experiences negative side-effects from treatment with commonly used drugs for the treatment of bone disease, such as bisphosphonates.

As used herein, and as well understood in the art, "treating" or "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease or disorder, preventing spread of disease or disorder, delay or slowing of disease or disorder progression, amelioration or palliation of the disease or disorder state, and remission (whether partial or total), whether detectable or undetectable. "Treatment" can also mean prolonging survival as compared to expected survival if not receiving treatment. In one embodiment, treatment refers to reducing bone resorption in a subject with bone disease such as to reduce or eliminate any undesirable physiological effects associated with resorptive bone disease such as bone pain. In one embodiment, treatment of subjects in need thereof with the peptides described herein may result in a reduced risk of bone fractures, reduced need for bone surgery, reduced need for bone radiotherapy, a reduced occurrence of spinal cord compression and/or hypercalcemia.

Optionally the peptides described herein can be formulated into a pharmaceutical composition for administration to subjects in a biologically compatible form suitable for use in vivo. The term "biologically compatible form suitable for administration in vivo" refers to a form of the substance to be administered in which any toxic effects are outweighed by the therapeutic effects. The peptides may be administered to living organisms including humans and animals.

Administration of a therapeutically active amount of the peptides or pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of the substance to elicit a desired response in the individual. Dosage regimes may be adjusted to provide the optimum therapeutic response. For example, several divided doses may be administered daily or the dose may be proportionally reduced as indicated by the exigencies of the therapeutic situation.

The peptides of the invention are preferably combined with other components such as a carrier in a composition such as a pharmaceutical composition or cosmetic composition. The compositions are useful when administered in methods for the treatment or prevention of bone disease. Optionally, the peptides described herein are administered with therapeutic compounds or other substances that are known to cause bone disease to moderate bone resorption such as, but not limited to, corticosteroids and/or estrogen- or testosterone-lowering therapies.

The peptides or pharmaceutical compositions can be administered to humans or animals by a variety of methods including, but not restricted to topical administration, oral administration, aerosol administration, intratracheal instillation, intraperitoneal injection, injection into the cerebrospinal fluid, intravenous injection and subcutaneous injection. Dosages to be administered depend on patient needs, on the desired effect and on the chosen route of administration. Nucleic acid molecules encoding for the peptides and polypeptides described herein may be introduced into cells using in vivo delivery vehicles such as liposomes, They may also be introduced into these cells using physical techniques such as microinjection and electroporation or chemical methods such as coprecipitation or using liposomes.

The pharmaceutical compositions are prepared by known methods for the preparation of pharmaceutically acceptable compositions which can be administered to patients, and such that an effective quantity of the peptide is combined in a mixture with a pharmaceutically acceptable vehicle. Suitable vehicles are described, for example in Remington's Pharmaceutical Sciences (Remington's Pharmaceutical Sciences, Mack Publishing Company, Easton, Pa., USA) or Handbook of Pharmaceutical Additives (compiled by Michael and Irene Ash, Gower Publishing Limited, Aldershot, England (1995). On this basis, the compositions include, albeit not exclusively, solutions of the substances in association with one or more pharmaceutically acceptable vehicles or diluents, and may be contained in buffered solutions with a suitable pH and/or be iso-osmotic with physiological fluids. In one embodiment, there is provided a composition comprising a peptide as described herein for reducing bone resorption and/or osteoclast activity and a pharmaceutically acceptable vehicle or diluent.

The following examples illustrate embodiments of the invention and do not limit the scope of the invention.

EXAMPLES

Materials & Methods

In-Vitro Generation of Human Osteoclasts

Osteoclasts were generated in vitro by the modified method of Cody et al., 2011, using fresh human bone marrow aspirates. Briefly, bone marrow mononuclear cells (BMC) separated on a density gradient medium in SepMate tubes were resuspended in growth media (α-MEM with 10% FBS) and cultured for 3 days in T75 flask with 35 ng/mL M-CSF at 37° C. in a 5% CO2 incubator. For osteoclast differentiation experiments, $10^5$ cells/well of BM monocytes-macrophage precursors seeded in a 24 well plate was treated with human M-CSF and RANKL, and media replenished with fresh cytokines every third day for two weeks.

Osteoclast Characterization

Osteoclasts were fixed and stained for tartrate-resistant acid phosphatase (TRAP) using the leukocyte acid phosphatase kit (Sigma-Aldrich) according to the manufacturer's protocol. Images were acquired in EVOS brightfield microscope. To visualize actin ring formation in osteoclasts, tetramethyl rhodamine-phalloidin (Life Technologies Inc.) staining was done for 1 hour. The cell nuclei were counterstained with 1 μg/ml Hoechst 33342 (Sigma-Aldrich) in phosphate buffered saline for 5 minute. Images were acquired in EVOS fluorescence microscope. TRAP enzyme activity was measured at 37° C. with a substrate buffer (125 mg/ml Naphthol AS-BI phosphoric acid in diazotized fast garnet base chemical solution, Sigma-Aldrich) at 560 nm.

Western Blotting

Proteins were extracted using RIPA buffer (50 mM Tris HCL pH 7.4, 150 mM NaCl, 1% NP-40, 0.25% Na-deoxycholate, 1 mM PMSF), sonicated for 15 s at 30% amplitude, incubated in ice for 30 min followed by centrifugation at 4° C. for 30 min at 1200 g. Protein concentration in supernatants was quantified using Pierce™ BCA Protein Assay kit (Thermo Scientific, IL, USA). 25 μg of protein extracts mixed with Laemmli sample buffer with 5% β-mercapto ethanol and boiled for 5 min at 95° C. were resolved by SDS-PAG electrophoresis on mini-Protean™ TGX Stain-Free® any kD gel, subsequently transferred onto PVDF membrane by semi dry method using Trans-Blot® Turbo™

Transfer system (25 Volts (V), 10 minute transfer). The membrane was then washed with TBS-T buffer (Tris.HCl, pH 7.5, 140 mM NaCl, and 0.05% Tween 20), blocked in 5% skimmed milk for 1 h and incubated overnight at 4° C. with specific primary antibody such as anti-rabbit TRPV6 Ab (Alomone, ACC-036, 1:500; and Santacruz, H-90, 1:500) or Cathepsin K (Abcam, 1:200). Proteins in immunoblots were detected with Amersham™ ECL™ Prime western blotting detection kit and imaged in a ChemiDoc™ MP imaging system (Bio-Rad Technology, CA, USA) with the Image Lab 5.0 software.

Immunohistochemistry

Paraffin embedded human bone specimen was sectioned at 5 μm thickness, decalicified and subjected to automated IHC staining in Ventana Benchmark Ultra Platform. Heat induced epitope retrieval was done with high pH solution for 36 min, followed by anti-TRPV6 primary antibody incubation (Alomone ACC-036; 1:200) for 32 min. Following diamino benzidine detection, sections were counterstained with hematoxylin. Images were acquired in Leica Microscope with LAS 4.6 Software.

Osteoclast Differentiation and Osteoassay $10^5$ BMCs per well in 24 well Corning osteoassay plate were treated with human M-CSF (10 ng/mL) and 10 ng/mL of human RANKL. Undifferentiated condition includes cells treated with M-CSF only. The treatment wells had both M-CSF and RANKL followed by addition of TRPV6 peptide antagonists SOR-C13 and SOR-C27 at concentrations range 1 μM-150 μM tested in triplicate wells, vehicle or PBS buffer in which the peptides are dissolved and the standard anti-resorbing agent, Zoledronate were included for the experiment. Replenishment with fresh media containing M-CSF, RANKL and SOR peptides in respective wells was carried out every third day. On day 12, cells in osteoplates were removed by incubating with 10% bleach for 10 minutes; wells were washed with distilled water three times and air-dried for 3-5 hrs. Osteoassay plate was scanned using ChemiDoc MP and area of resorption pits in each well was quantified using ImageJ 1.48v Software.

Statistics

Experiments were done in triplicates for each condition and data presented as mean±SD. All statistical analyses were done using GraphPad Prism 6, one way ANOVA and Dunnett's multiple comparison test was used to determine significance between groups and $P<0.05$ is considered statistically significant.

Expression and Localization of TRPV6 in Osteoclasts

Figure 1:
FIG. 1 shows TRPV6 protein expression in human osteoclasts and myeloma cells.

Strong expression of TRPV6 in human osteoclasts was found by immunohistochemical staining (FIG. 1). Osteoclasts were generated in vitro by the modified method of Cody et al., 2011, using fresh bone marrow (BM) aspirates. BM aspirates and cultured bone marrow mononuclear cells were processed for two weeks by treatment with two key cytokines human M-CSF and RANKL essential for osteoclast differentiation.

Figure 2:
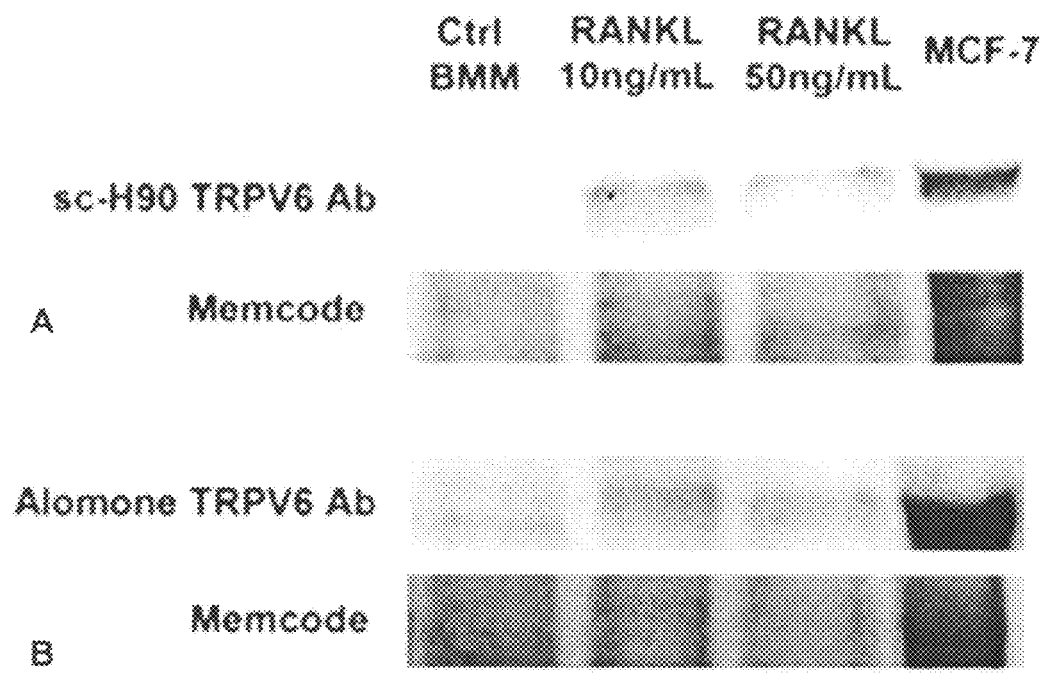
FIG. 2 shows TRPV6 protein expression in primary human osteoclast cultures. Proteins were extracted from undifferentiated BMCs, differentiated osteoclasts (10 ng/ml and 50 ng/ml RANKL treated conditions) and the positive control cells, MCF-7.
Figure 3:
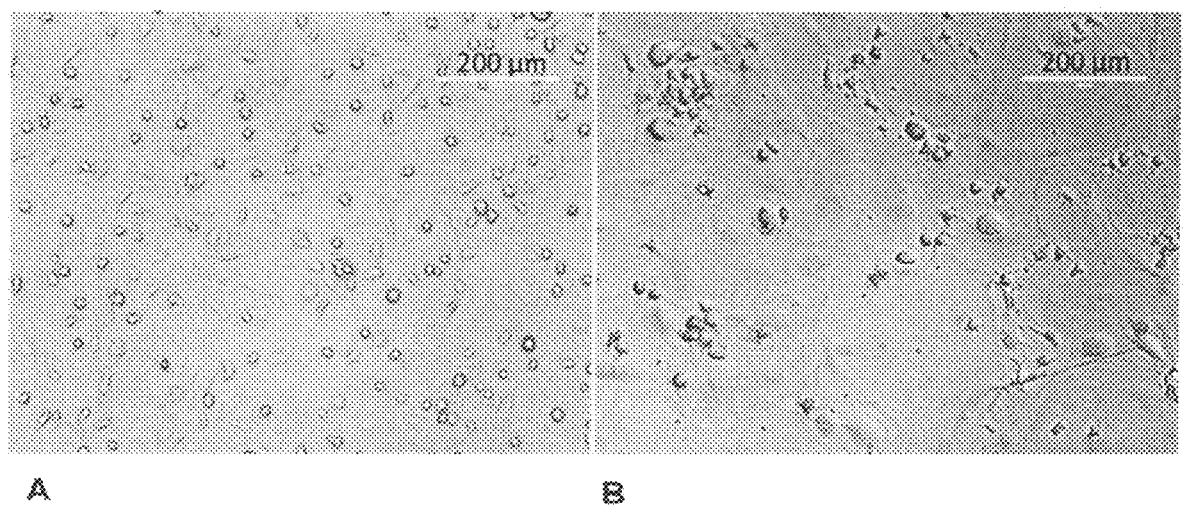
FIG. 3 shows phase contrast images of in vitro generated human osteoclasts.
Figure 4:
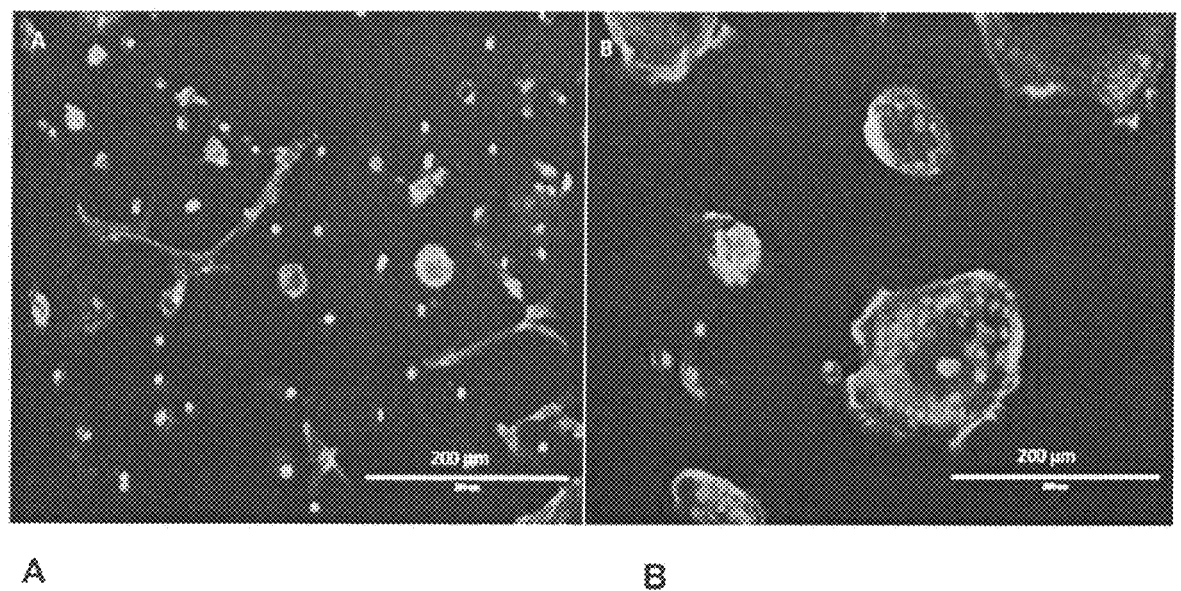
FIG. 4 shows phalloidin and hoechst staining of in vitro generated human osteoclasts.
Figure 5:
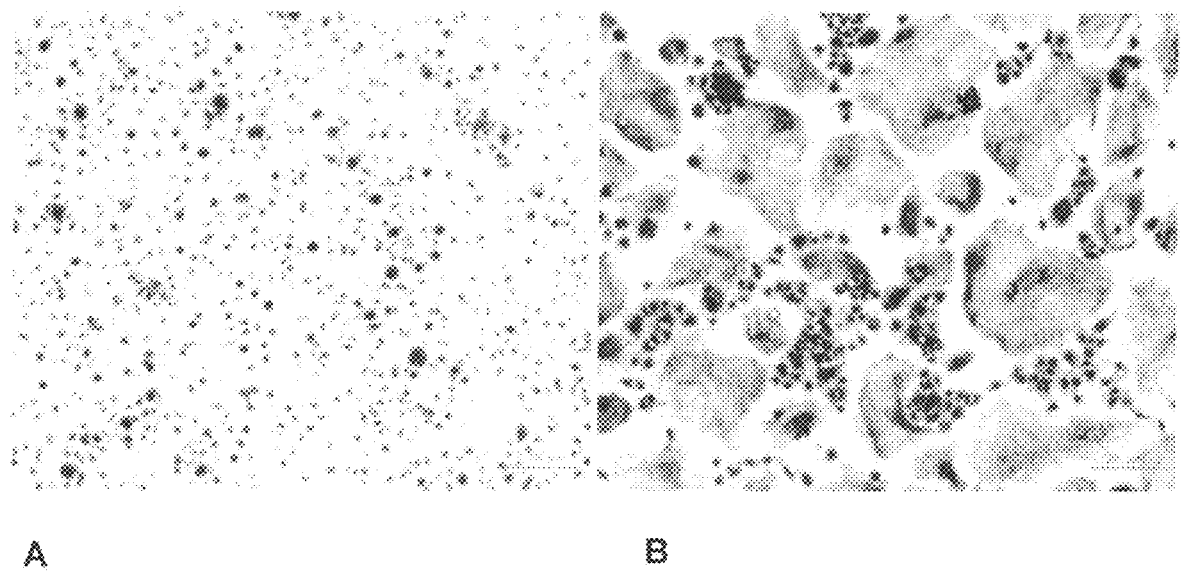
FIG. 5 shows tartrate-resistant acid phosphatase (TRAP) staining of in vitro generated human osteoclasts.
Figure 6:
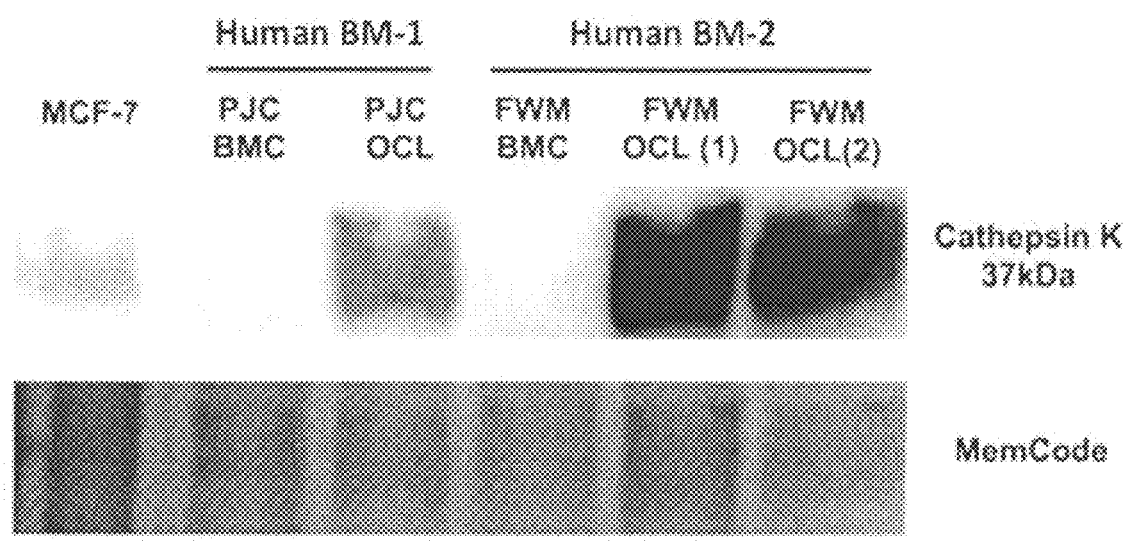
FIG. 6 shows Cathepsin K protein expression by human osteoclasts in vitro. Proteins extracted from undifferentiated BMCs, differentiated osteoclasts (OCL (1) and (2) are 10 ng/ml and 50 ng/ml RANKL treated conditions) and the positive control cells, MCF-7 were electrophoresed on a 4-20% gradient gel and transferred to PVDF membrane. Top panel is the immunoblot shows strong expression of Cathepsin K specifically in osteoclasts; bottom panel shows MemCode protein staining.

Osteoclast formation was observed from the sixth day onwards. The cells thus generated in vitro exhibited phenotypic characteristics of osteoclasts such as being large sized, multi-nucleated cells with actin rings. This is evident from the phase contrast image and the phalloidin & hoechst stained, fluorescence microscope images of osteoclasts (FIGS. 3b and 4b). These osteoclasts were found to strongly express bone resorption markers such as Tartarate-resistant acid phosphatase (FIG. 5), Cathepsin K (FIG. 6), also exhibit their characteristic functional activity of resorbing osteoassay surface (FIG. 7). Furthermore, the osteoclasts generated from primary human bone marrow expressed TRPV6 protein as determined by western blotting (FIG. 2).

Effect of C-Terminal Soricidin Peptides on Osteoclasts

The effect of C-terminal Soricidin peptides on osteoclast activity and bone resorption was examined using 24-well corning assay plates that have a 3D osteo surface that mimics in vivo bone for in vitro bone cell assays. The inorganic bone biomaterial surface in each well is capable of supporting the functional properties of osteogenic cells. Only osteoclasts, specialized cells expressing bone-resorbing enzymes such as TRAP, cathepsin K and collagenase, can resorb such an artificial osteosurface. Resorption of the osteosurface is evident from the resorption pits/trails made by the osteoclasts, and the extent of resorption was quantified. Furthermore, the percentage activity of TRAP, one of the enzymes involved in bone resorption, was determined in tandem with the resorption assay (FIG. 7c). The anti-resorptive potential of selective TRPV6 antagonist peptides, SOR-C13 and SOR-027 at various concentrations was observed (FIGS. 7 and 8) was observed. At a concentration of 150 μM (C5) a consistent, significant effect was observed where the peptides inhibited osteoclast differentiation in vitro, and significantly reduced their resorptive activity on corning osteoassay surface.

Figure 9:
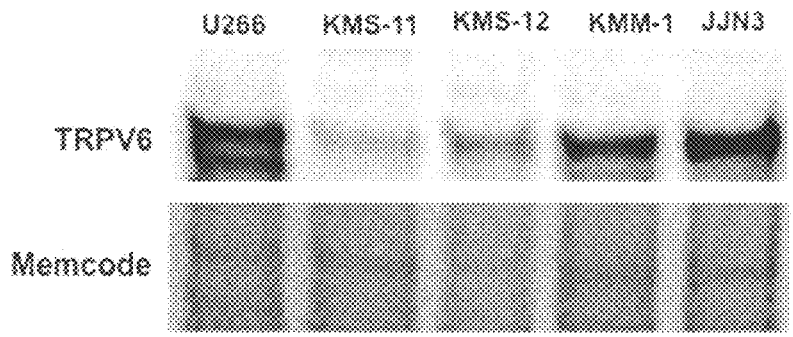
FIG. 9 shows expression of TRPV6 in human myeloma cell lines. The top panel shows an immunoblot showing strong TRPV6 protein expression in human myeloma cell lines; the bottom panel shows MemCode protein staining.
Figure 10:
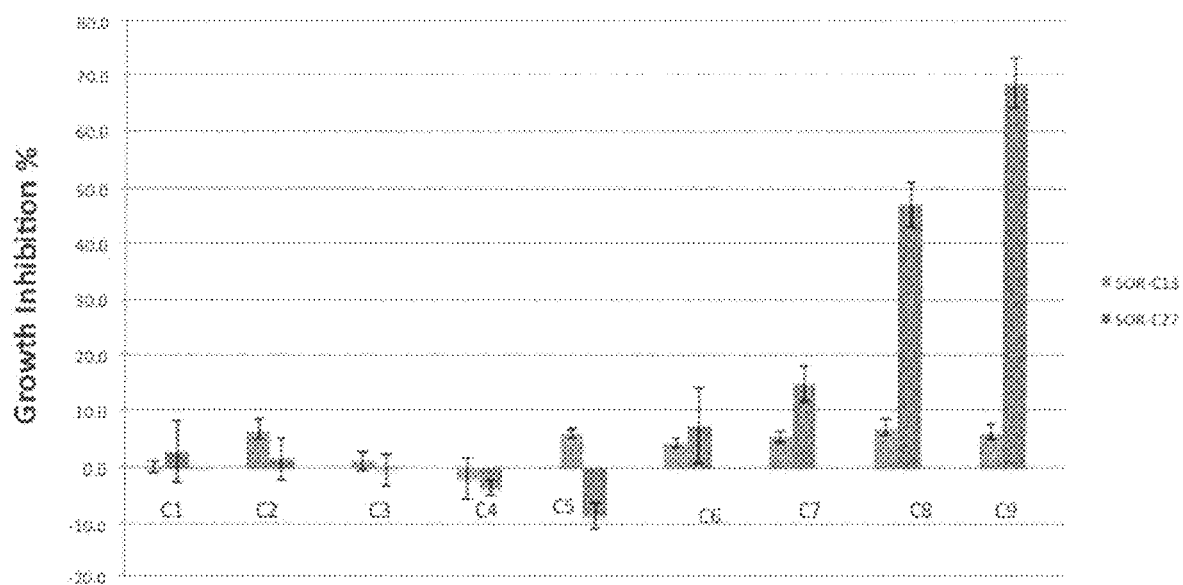
FIG. 10 shows the results of a 48 hr TRPV6 antagonist peptide treatment on a human myeloma cell line (KMM-1 cells). A dose-dependent inhibition of cell growth was observed with increasing concentrations of SOR C-13 and SOR-C27. C1=1 uM; C2=10 uM; C3=50 uM; C4=100 uM; C5=150 uM; C6=250 uM; C7=300 uM; C8=400 uM; C9=500 uM.
Figure 11:
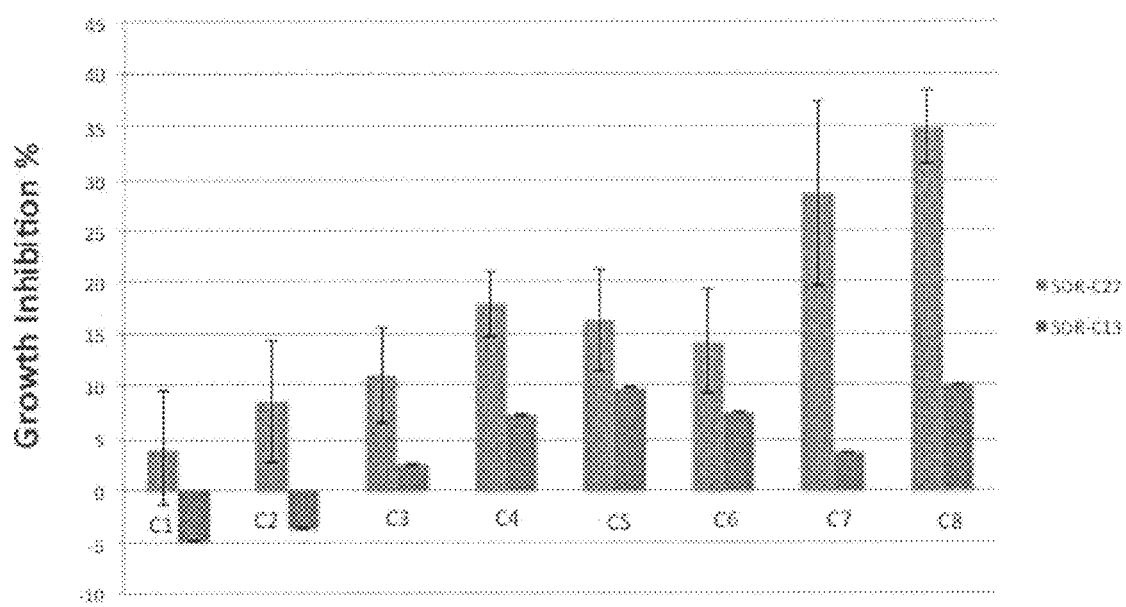
FIG. 11 shows the results of 48 hr TRPV6 antagonist peptide treatment on human myeloma cell line (U266 cells). A dose-dependent inhibition of cell growth was observed with increased concentrations of SOR C-13 and SOR-C27. C1=1 uM; C2=10 uM; C3=50 uM; C4=100 uM; C5=150 uM; C6=250 uM; C7=400 uM; C8=500 uM.

The expression of TRPV6 protein was also observed in human myeloma cells by immunohistochemistry on myeloma bone sections (FIG. 10) and in myeloma cell lines by western blotting (FIG. 9). Moreover, the growth inhibitory potential of SOR-C13 and SOR-027 was determined using human myeloma cell lines U266 and KMM-1 (FIGS. 10 and 11). There exists a reciprocal relationship between myeloma cells and osteoclasts in the bone marrow milieu where myeloma cells secrete many factors that promote osteoclast activity, and in turn osteoclasts induce myeloma cell growth and survival. Hence, along with the anti-resorptive property, the myeloma cell growth inhibitory property of SOR-C13 and SOR-C27 can be applied for treating myeloma bone disease.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

The invention claimed is:

1. A method for treating or preventing resorptive bone disease in a human subject in need thereof, comprising administering to the subject a peptide comprising the amino acid sequence KEFLHPSKVDLPR (SEQ ID NO:1).

2. The method of claim 1, wherein the peptide consists of the amino acid sequence of EGKLSSNDTEGGLCK-EFLHPSKVDLPR (SEQ ID NO: 2).

3. The method of claim 1, wherein the peptide consists of the amino acid sequence KEFLHPSKVDLPR (SEQ ID NO: 1) or EGKLSSNDTEGGLCKEFLHPSKVDLPR (SEQ ID NO: 2).

4. The method of claim 1, wherein the peptide inhibits osteoclast activity.

5. The method of claim 1, wherein the peptide inhibits bone resorption.

6. The method of claim 1, wherein the subject has osteoporosis, Paget's disease of bone or bone metastases.

7. The method of claim 1, wherein the subject has resorptive bone disease associated with multiple myeloma.

8. A method for inhibiting osteoclast activity comprising contacting one or more osteoclasts with a peptide comprising the amino acid sequence KEFLHPSKVDLPR (SEQ ID NO:1).

9. The method of claim 8, wherein the peptide consists of the amino acids sequence EGKLSSNDTEGGLCK-EFLHPSKVDLPR (SEQ ID NO: 2).

10. The method of claim 8, wherein the peptide comprises the amino acid sequence EGKLSSNDTEGGLCK-EFLHPSKVDLPR (SEQ ID NO: 2).

11. The method of claim 8, wherein the peptide consists of the amino acid sequence KEFLHPSKVDLPR (SEQ ID NO: 1) or EGKLSSNDTEGGLCKEFLHPSKVDLPR (SEQ ID NO: 2).

12. The method of claim 8, wherein the osteoclasts are in vivo or in vitro.

13. The method of claim 8, wherein the osteoclasts are in contact with bone and contacting the osteoclasts with the peptide inhibits bone resorption.

14. The method of claim 8, wherein the peptide inhibits osteoclast differentiation.

15. The method of claim 1, wherein the osteoclasts express Transient Receptor Potential Vanilloid channel 6.

16. The method of claim 8, wherein the osteoclasts activity has been increased by osteoclast activating factors secreted by one or more myeloma cells.

\* \* \* \* \*